United States Patent [19]

Woltersdorf, Jr. et al.

[11] Patent Number: 4,777,281

[45] Date of Patent: Oct. 11, 1988

[54] [3,4-DICHLORO-6,7,8,8A,9,10-HEXAHYDRO-6-OXO-8A-SUBSTITUTED-2-PHENAN-THRENYL)OXY]-ALKANOIC ACIDS AND -ETHANIMIDAMIDES

[75] Inventors: Otto W. Woltersdorf, Jr., Chalfont; Edward J. Cragoe, Jr., Lansdale, both of Pa.

[73] Assignee: Merck & Co., Inc., Rahway, N.J.

[21] Appl. No.: 835,599

[22] Filed: Mar. 3, 1986

[51] Int. Cl.$^4$ ............................................. C07C 69/76
[52] U.S. Cl. ..................................... 560/53; 562/461; 564/245
[58] Field of Search ................... 560/651, 53; 562/461; 564/245; 574/543, 569, 657

[56] References Cited

PUBLICATIONS

"Agents for the Treatment of Brain Injury" 1. (Aryloxy) Alkanoic Acids, Cragoe, et al., J. Med. Chem. (1982) 25 567–579.

*Primary Examiner*—Paul J. Killos
*Attorney, Agent, or Firm*—Charles M. Caruso; Hesna J. Pfeiffer

[57] ABSTRACT

The invention relates to novel [(3,4-dichloro-6,7,8,8a,9,10-hexahydro-6-oxo-8a-substituted-2-phenanthrenyl)ox yl]-alkanoic acids and -ethanimidamides and their salts. The compounds are useful for the treatment and prevention of injury to the brain and of edema due to head trauma, stroke (particularly ischemic), arrested breathing, cardiac arrest, Reye's syndrome, cerebral thrombosis, cerebral embolism, cerebral hemorrhage, cerebral tumors, encephalomyelitis, spinal cord injury, hydrocephalus, post-operative brain injury trauma, edema due to cerebral infections and various brain concussions.

7 Claims, No Drawings

[3,4-DICHLORO-6,7,8,8A,9,10-HEXAHYDRO-6-OXO-8A-SUBSTITUTED-2-PHENANTHRENYL-)OXY]-ALKANOIC ACIDS AND -ETHANIMIDAMIDES

BACKGROUND OF THE INVENTION

Trauma to the brain or spinal cord caused by physical forces acting on the skull or spinal column, by ischemic stroke, arrested breathing, cardiac arrest, Reye's syndrome, cerebral thrombosis, cerebral embolism, cerebral hemorrhage, encephalomyelitis, hydrocephalus, post-operative brain injury, cerebral infections and various concussions results in edema and swelling of the affected tissues. This is followed by ischemia, hypoxia, necrosis, temporary or permanent brain and/or spinal cord injury and may result in death. The tissue mainly affected are classified as grey matter, more specifically astroglial cells. The specific therapy currently used for the treatment of the medical problems described include various kinds of diuretics (particularly osmotic diuretics), steroids (such as, 6-α-methylprednisolone succinate) and barbiturates. The usefulness of these agents is questionable and they are associated with a variety of untoward complications and side effects. Thus, the compounds of this invention comprise a novel and specific treatment of medical problems where no specific therapy is available.

A recent publication entitled "*Agents for the Treatment of Brain Injury*" 1. (Aryloxy)alkanoic Acids, Cragoe et al, J. Med. Chem., (1982) 25, 567–79, reports on recent experimental testing of agents for treatment of brain injury and reviews the current status of treatment of brain injury.

The compounds of the invention have the added advantage of being essentially devoid of the pharmacodynamic, toxic or various side effects characteristic of the diuretics, steroids and barbiturates.

DESCRIPTION OF THE INVENTION

The compounds of the instant invention are best characterized by reference to the following structural Formula (I):

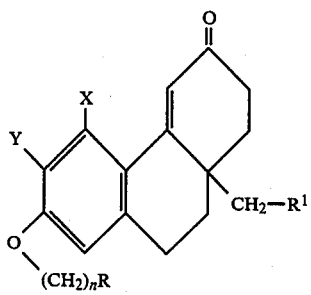

wherein:
R is COOH, COOR² or

R¹ is H, lower alkyl, branched or unbranched, containing from 1 to 5 carbon atoms such as methyl, ethyl, propyl, isopropyl and the like, aryl such as phenyl, halo substituted aryl such as p-fluorophenyl, o-fluorophenyl, p-chlorophenyl and the like, aralkyl such as benzyl, cycloalkyl containing from 3 to 6 nuclear carbon atoms such as cyclopropyl, cyclobutyl, cyclopentyl and the like, or cycloalkyl-lower alkyl containing from 4 to 7 total carbon atoms such as cyclopentylmethyl and the like;

R² is a lower alkyl group containing from 1 to 5 carbon atoms, or a carboxyalkyl group containing from 2 to 6 carbon atoms such as carboxymethyl, 1-carboxyethyl, 1-carboxy-1-methylethyl, 2-carboxyethyl, 1-carboxy-1-ethylpropyl and the like;

R³ is NH₂, NHR⁵ or NR⁵R⁶;

R⁴ is NH or NR⁵;

R⁵, R⁶ are each independently lower alkyl, branched or unbranched, containing from 1 to 5 carbon atoms, or amino, provided that R⁵ and R⁶ are not both amino;

wherein R³ and R⁴ may be joined together via R⁵ to form a heterocyclic ring of 5 or 6 atoms containing 2 nitrogen atoms and 3 or 4 carbon atoms, such as:

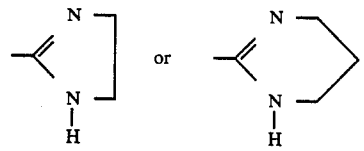

or wherein R⁵ and R⁶ may be joined together to form a 5- or 6-membered ring containing one nitrogen atom and 4 or 5 carbon atoms, such as:

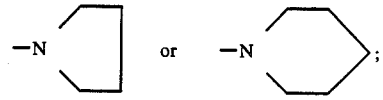

X and Y are hydrogen, halo or lower alkyl, containing from 1 to 5 carbon atoms; and n is 1 to 4.

Since the 8a carbon atom in the molecule is asymmetric, the compounds of the invention are racemic. However, these compounds or their precursors can be resolved so that the pure enantiomers can be prepared, thus the invention includes the pure enantiomers. This is an important point since some of the racemates consist of one enantiomer which is much more active than the other one. Furthermore, the less active enantiomer generally possesses the same intrinsic toxicity as the more active enantiomer. In addition, it can be demonstrated that the less active enantiomer depresses the inhibitory action of the active enantiomer at the tissue level. Thus, for three reasons it is advantageous to use the pure, more active enantiomer rather than the racemate.

Since the products of the invention where R is COOH are acidic, the invention also includes the obvious pharmaceutically acceptable salts, such as the sodium, potassium, ammonium, trimethylammonium, piperazinium, 1-methylpiperazinium, guanidinium, bis-(2-hydroxyethyl)ammonium, N-methylglucosammonium and the like salts.

Since the products of the invention where R is

are basic, the invention includes the obvious pharmaceutically acceptable salts, such as the hydrochloride, methanesulfonate, isethionate, maleate, succinate, acetate and the like salts.

It is also to be noted that the compounds of Formula I, as well as their salts, often form solvates with the solvents in which they are prepared or from which they are recrystallized. These solvates may be used per se or they may be desolvated by heating (e.g. at 70° C.) in vacuo.

Although the invention primarily inolves novel [(3,4-dichloro-6,7,8,8a,9,10-hexahydro-6-oxo-8a-propyl-2-phenanthrenyl)oxy]-alkanoic acids and ethanimidamides and their salts, it also includes their derivatives, such as esters, amides, oximes, hydrazones and the like. Additionally, this invention includes pharmaceutical compositions in unit dosage form containing a pharmaceutical carrier and an effective amount of a compound of Formula I, its pure diasteriomer and its pure (−) or (+) enantiomer, or the pharmaceutically acceptable salts thereof, for treating brain injury. The method of treating a person with brain injury by administering said compounds or said pharmaceutical compositions is also a part of this invention.

PREFERRED EMBODIMENT OF THE INVENTION

The preferred embodiments of the instant invention are realized in structural Formula II:

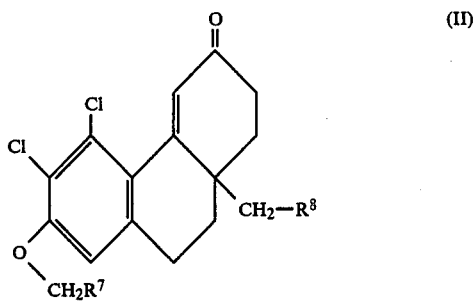

wherein:
$R^7$ is COOH, COOR$^9$ or

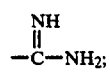

$R^8$ is H, lower alkyl, branched or unbranched; containing from 1 to 5 carbon atoms;
$R^9$ is a carboxyalkyl group containing from 2 to 6 carbon atoms such as carboxymethyl, 1-carboxyethyl, 1-carboxy-1-methylethyl, 2-carboxyethyl, 1-carboxy-1-ethylpropyl and the like.

Also included are the enantiomers of each racemate.

A preferred compound is [(3,4-dichloro-6,7,8,8a,9,10-hexahydro-6-oxo-8a-propyl-2-phenanthrenyl)oxy]acetic acid.

Also preferred is 2-[(3,4-dichloro-6,7,8,8a,9,10-hexahydro-6-oxo-8a-propyl-2-phenanthrenyl)oxy]ethanimidamide hydrochloride.

Especially preferred are the pure enantiomers since, in most instances, one enantiomer is more active biologically then its antipode.

Included within the scope of this invention are the pharmacologically acceptable salts of the [(3,4-dichloro-6,7,8,8a,9,10-hexahydro-6-oxo-8a-substituted-2-phenanthrenyl)oxy]-alkanoic acids and ethanimidamides, since a major medical use of these compounds is solutions of their soluble salts which can be administered parenterally.

Thus, the acid addition salts of the compounds of this invention where R is COOH can be prepared by the reaction of the [(3,4-dichloro-6,7,8,8a,9,10-hexahydro-6-oxo-8a-substituted-2-phenanthrenyl)oxy]alkanoic acids of this invention with an appropriate amine, such as, ammonium hydroxide, guanidine, alkali metal hydroxide, alkali metal carbonate, alkali metal bicarbonate, quaternary ammonium hydroxide and the like. The salts selected are derived from among the non-toxic, pharmaceutically acceptable bases.

Likewise, the salts of compounds of this invention where R is

can be prepared by the reaction of the 2-[(3,4-dichloro-6,7,8,8a,9,10-hexahydro-6-oxo-8a-substituted-2-phenanthrenyl)oxy]ethanimidamides of this invention with an appropriate pharmaceutically acceptable acid, such as, hydrochloric acid, sulfuric acid, acetic acid, maleic acid, isethionic acid, methanesulforic acid, succinic acid and the like.

The synthesis of the [(3,4-dichloro-6,7,8,8a,9,10-hexahydro-6-oxo-8a-substituted-2-phenanthrenyl)oxy]alkanoic acids of formula Ia are generally carried out by the route illustrated below.

SCHEME I

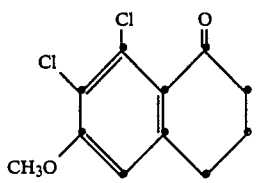

(III)

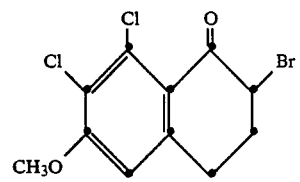

(IV)

SCHEME I -continued
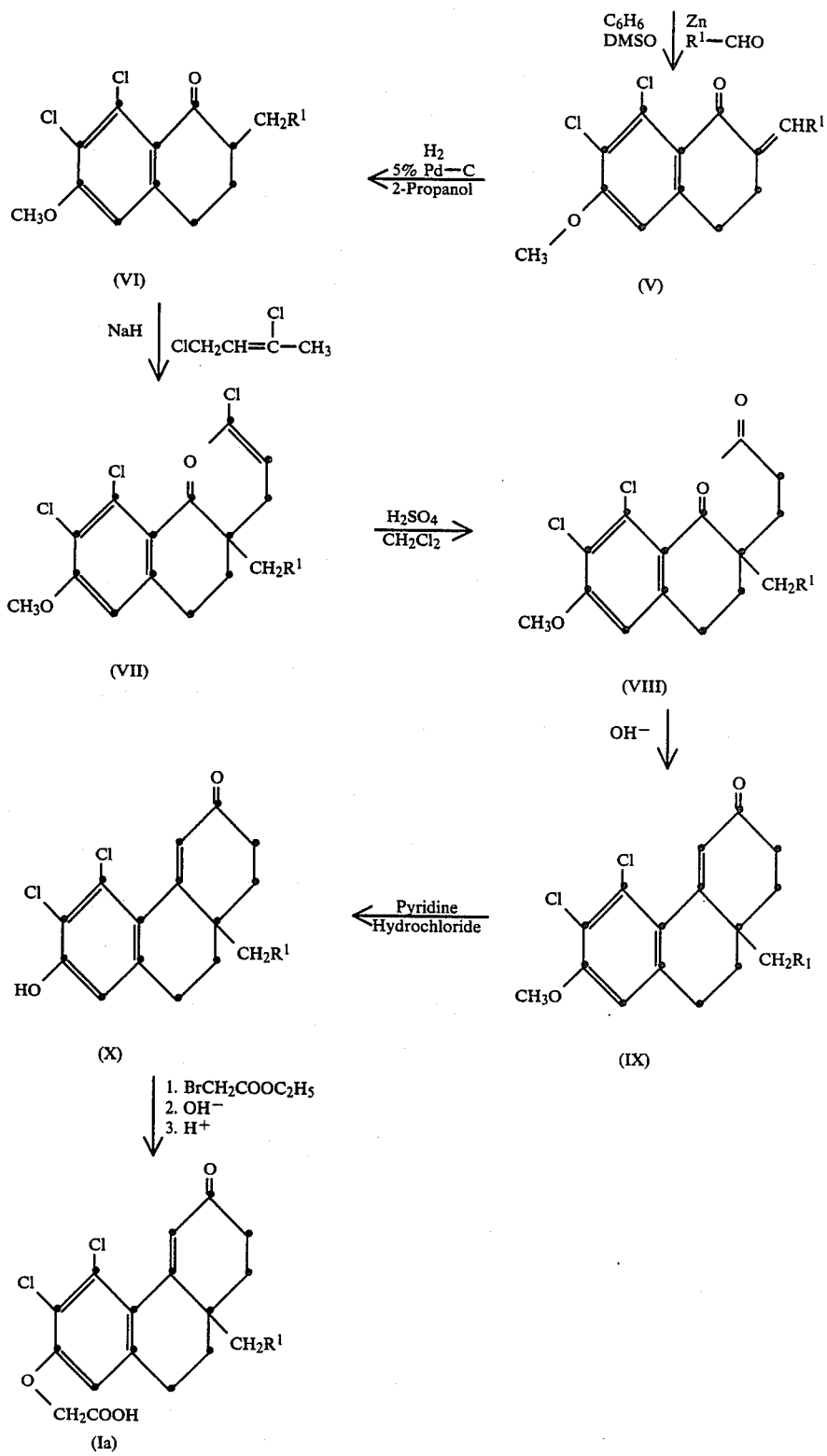
Bromination of compounds of Formula III in a solvent such as acetic acid gives the bromo derivatives of Formula IV which upon treatment with an aldehyde of Formula R¹CHO in the presence of zinc dust yields compounds of Formula (V). The reaction is conveniently conducted in a solvent mixture compound of benzene and dimethyl sulfoxide. The double bond of a compound of Formula V is readily reduced with hydrogen in the presence of a catalyst such as 5% palladium on carbon to produce a ketone of Formula VI. The reduction is conveniently conducted using a Parr apparatus at 20 to 40 psi of hydrogen gas.

Alkylation of a compound of Formula VI was accomplished by first reacting it with sodium hydride in a mixture of toluene and dimethylformamide followed by reaction with 1,3-dichloro-2-butene. The product of this reaction is a compound of Formula VII which upon reaction with sufuric acid in methylene chloride produces a compound of Formula VIII upon quenching with water.

Conversion of a compound of Formula VIII to a compound of Formula IX is accomplished by stirring a compound of Formula VIII in a solution of aqueous-alcoholic sodium hydroxide for a period of 70 to 120 hours at a temperature of 15° to 30° C. Heating a compound formula IX in molten pyridine hydrochloride at a temperature of 170°-190° C. for a period of 30 to 90 minutes produces a phenol of Formula X.

The reaction of a phenol of Formula X with ethyl bromoacetate in the presence of potassium carbonate, using a solvent, such as dimethylformamide at a temperature of 50° to 70° C. produces the ethyl ester of a compound of Formula Ia. Hydrolysis of this ester is accomplished by stirring it with an aqueous methanolic sodium hydroxide at ambient temperature for a period of 30 minutes to 2 hours. Acidification of the solution with an acid, such as hydrochloric acid, produces a compound of Formula Ia.

The synthesis of the 2-[(3,4-dichloro-6,7,8,8a,9,10-hexahydro-6-oxo-7-substituted-8a-substituted-2-phenanthrenyl)oxy]ethanimidamides salts of Formula Ib can be accomplished by one of several methods. According to one method, a phenol of Formula X (as described in Example 2, Step F) is reacted with chloroacetonitrile in the presence of potassium carbonate in a solvent, such as dimethylformamide. The reaction is carried out at a temperature of 50° to 75° C. for a period of one to four hours to obtain a nitrile of Formula XI. The nitrile of Formula XI is then reacted with methanol containing some sodium methoxide to obtain an imino ester of Formula XII which is generally used directly without isolation. The reaction is generally carried out at ambient temperature (15° to 30° C.) for a period of 30 minutes to 5 hours.

The reaction of imino ester of Formula XII with an ammonium salt or amine salt of Formula $HNR^6R^7$; HX give the compound of Formula Ib.

Scheme II.

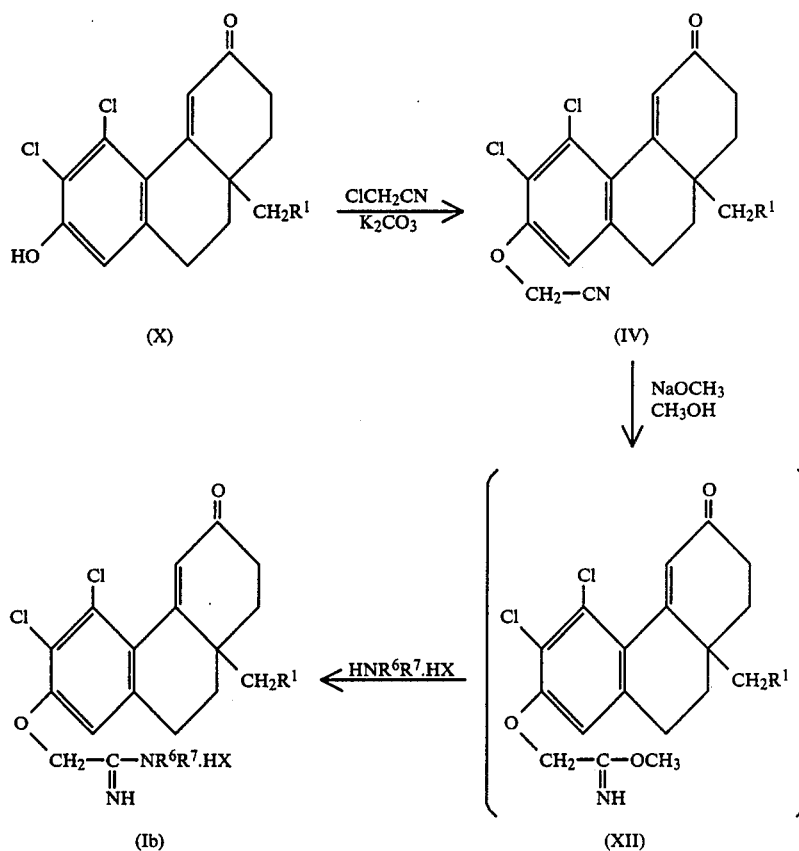

The reaction is conducted in situ in the methanol solvent in which the compound of Formula XII was generated. The reaction is generally conducted at ambient temperatures (15° to 30° C.) for a period of two to 10 hours. The salt of Formula Ib can be isolated and purified per se or it may be converted to the free base by addition of an inorganic base such as sodium hydroxide or potassium hydroxide, in cold water, extracted with an organic solvent, such as ether, dried and converted into the desired salt by the addition of a pharmaceutically acceptable acid. Acids, such as hydrochloric acid, hydrobromic acid, acetic acid, maleic acid, isethionic acid, methanesulfonic acid, sulfuric acid and the like can be used.

One method of preparing pure enantiomers of Formula Ib is to take the pure enantiomers of Ia, i.e. those of Formula (+)Ia and (−)Ia cleave them to the corresponding enantiomers of the phenol X, i.e., those of Formula (+)X and (−)X. The phenol of Formula (+)X and (−)X are then used in the sequence of reactions shown in Scheme II to produce the 2-[(3,4-dichloro-6,7,8,8a,9,10-hexahydro-6oxo-8a-substituted-2-phenanthrenyl)oxy]ethanimidamides salts of Formula (+)Ib and (−)Ib as shown in Scheme III.

Scheme III

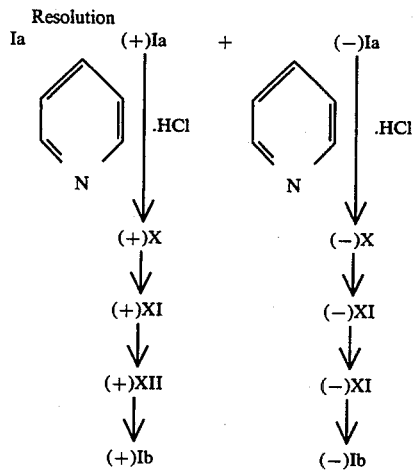

One method for the synthesis of esters of Ia where $R^7$ is $COOR^9$ (i.e., Formula XV) that is especially advantageous is illustrated below:

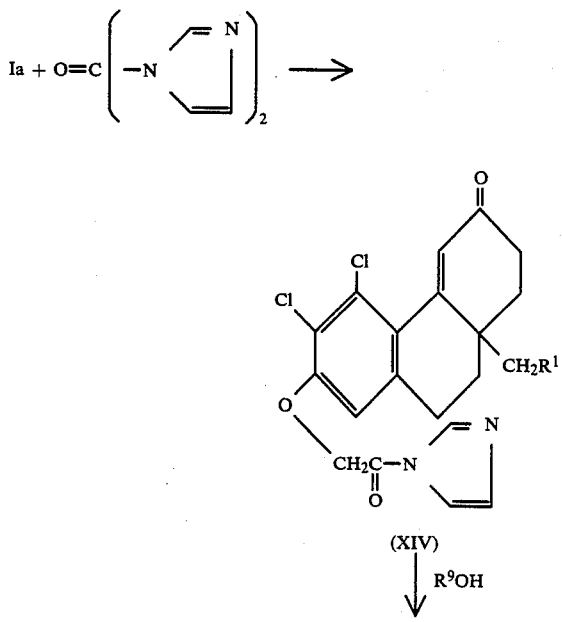

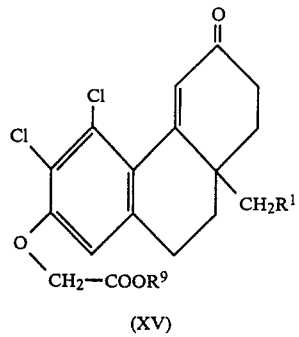

A carboxylic acid of Formula Ia is reacted with 1,1'-carbonyldiimidazole (XIII) in an inert solvent such as tetrahydrofuran to produce the acylimidazole derivative of Formula XIV. This intermediate may be isolated or reacted in situ with an alcohol of Formula $R^9OH$ to give the desired ester of Formula XV. This synthetic method is especially carboxy esters like the 1-carboxy-1-methylethyl esters of Examples 7 and 8.

Those acidic compounds (i.e. those where R=COOH) possessing an asymmetric carbon atom at positions 8a-position of the molecule consist of a racemate composed of two enantiomers. The resolution of each racemate may be accomplished by forming a salt of the racemic mixture with an optically active base such as (+) or (−)amphetamine, (−)cinchonidine, dehydroabietylamine, (+) or (−)--methylbenzylamine, (+) or (−) (1-naphthyl)ethylamine (+) cinchonine, brucine, or strychnine and the like in a suitable solvent such as methanol, ethanol, 2-propanol, benzene, acetonitrile, nitromethane, acetone and the like. There is formed in the solution, two diastereomeric salts, one of which is usually less soluble in the solvent than the other. Repetitive recrystallization of the crystalline salt generally affords a pure diastereomeric salt from which is obtained the desired pure enantiomer. The optically pure enantiomer of the compound of Formula I is obtained by acidification of the salt with a mineral acid, isolation by filtration and recrystallization of the optically pure antipode.

The other optically pure antipode may generally be obtained by using a different optically active base to form the ddiastereomeric salt. It is of advantage to isolate the partially resolved acid from the filtrates of the purification of the first diastereomeric salt and to further purify this substance through the use of another optically active base. It is especially advantageous to use an optically active base for the isolation of the second enantiomer which is the antipode of the base used for the isolation of the first enantiomer. For example, if (+)-α-methylbenzylamine was used first, then (−)-α-methylbenzylamine is used for the isolation of the second (remaining) enantiomer.

The compounds of the invention where $$R = -\overset{R^4}{\underset{||}{C}} - R^3$$

may be resolved in a similar way using optically active acids, i.e. (+) and (−) malic acid, (+) and (−) dibenzoyltartaric acid, (+) ad (−) α-methoxy-α(trifluoromethyl)phenylacetic acid, (+) and (−)-tartaric acid, 1- and d-10-camphorsufonic acid, 1- and d-α-bromocaphor-π-sulfonic acid and the like in a suitable solvent, such as methanol, ethanol, 2-propanol, acetonitrile, nitromethane and the like.

The salts of the carboxylic acids are prepared by reacting the acids of Formula I with an appropriate base, for example, alkali metal or alkaline earth becarbonate, carbonate or alkoxide, an amine, ammonia, an organic quaternary ammonium hydroxide, guanidine and the like.

The reaction is generally conducted in water when alkali metal hydroxides are used, but when alkoxides and the organic bases are used, the reaction may be conducted in an organic solvent, such as ether, ethanol, dimethylformamide and the like.

The preferred salts are the pharmaceutically acceptable salts such as sodium, potassium, ammonium and the like.

Inasmuch as there are a variety of symptoms and severity of symptoms associated with grey matter edema, particularly when it is caused by head trauma, stroke, cerebral hemorrhage or embolism, post-operative brain surgery trauma, spinal cord injury, cerebral infections and various brain concussions, the precise treatment is left to the practitioner. Generally, candidates for treatment will be indicated by the results of the patient's initial general neurological status, findings on specific clinical brain stem functions and findings on computerized axial tomography (CAT), nuclear magnetic resonance (NMR) or positron emission tomography (PET) scans of the brain. The sum of the neurological evaluation is presented in the Glascow Coma Score or similar scoring system. Such a scoring system is often valuable in selecting the patients who are candidates for therapy of this kind.

The compounds of this invention can be administered by a variety of established methods, including intravenously, intramuscularly, subcutaneously, or orally. The parenteral route, particularly the intravenous route of administration, is preferred, especially for the very ill and comatose patient. Another advantage of the intravenous route of administration is the speed with which therapeutic brain levels of the drug are achieved. It is of paramount importance in brain injury of the type described to initiate therapy as rapidly as possible and to maintain it through the critical time periods. For this purpose, the intravenous administration of drugs of the type of Formula I in the form of their salts is superior.

A recommended dosage range for treatment is expected to be from 0.05 mg/kg to 50 mg/kg of body weight as a single dose, preferably from 0.5 mg/kg to 20 mg/kg. An alternative to the single dose schedule is to administer a primary loading dose followed by a sustaining dose of half to equal the primary dose, every 4 to 24 hours. When this multiple dose schedule is used the dosage range may be higher than that of the single dose method. Another alternative is to administer an ascending dose sequence of an initial dose followed by a sustaining dose of 1½ to 2 times the initial dose every 4 to 24 hours. For example, 3 intravenous doses of 8, 12 and 16 mg/kg of body weight can be given at 6 hour intervals. If necessary, 4 additional doses of 16 mg/kg of body weight can be given at 12 hour intervals. Another effective dose regimen consists of a continuous intravenous infusion of from 0.05 mg/kg/hr to 3.0 mg/kg/hr. Of course, other dosing schedules and amounts are possible.

One aspect of this invention is the treatment of persons with grey matter edema by concomitant administration of a compound of Formula I or its salts, and an antiinflammatory steroid. These steroids are of some, albeit limited, use in control of white matter edema associated with ischemic stroke and head injury. Steroid therapy is given according to established practice as a supplement to the compound of Formula I as taught elsewhere herein. Similarly, a barbiturate may be administered as a supplement to treatment with a compound of Formula I.

The compounds of Formula I are utilized by formulating them in a pharmaceutical composition such as tablet, capsule or elixir for oral administration. Sterile solutions or suspensions can be used for parenteral administration. A compound or mixture of compounds of Formula I, or its physiologically acceptable salt, is compounded with a physiologically acceptable vehicle, carrier, excipient, binder, preservative, stabilizer, flavor, etc. in a dosage form as called for by accepted pharmaceutical practice.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection or infusion can be formulated according to conventional pharmaceutical practice by dissolving the active substance in a conventional vehicle such as wate, saline or dextrose solution by forming a soluble salt in water using an appropriate base, such as a pharmaceutically acceptable alkali metal hydroxide, alkali metal bicarbonate, ammonia, amine or guanidine. Alternatively, a suspension of the active substance in a naturally occurring vegetable oil like sesame oil, coconut oil, peanut oil, cottonseed oil, etc., or a synthetic fatty vehicle like ethyl oleate or the like may be formulated for injection or infusion. Buffer, preservatives, anti-oxidants and the like can be incorporated as required.

The basic premise for the development of agents for the treatment of brain injury of the types described is based on the studies in experimental head injury by R. S. Bourke et. al. (R. S. Bourke, M. A. Daze and H. K. Kimelberg, Monograph of the International Glial Cell symposium, Leige, Bel. Aug. 29-31, 1977 and references cited therein) and experimental stroke by J. H. Garcia et. al. (J. H. Garcia, H. Kalimo, Y. Kamijyo and B. F. Trump, Virchows Archiv. [Zellopath.], 25, 191 (1977).

These and other studies have shown that the primary site of traumatic brain injury is in the grey matter where the process follows a pattern of insult, edema, ischemia, hypoxia, neuronal death and necrosis followed, in many instances, by irreversible coma or death. The discovery of a drug that specifically prevents the edema would obviate the sequalae.

Experimental head injury has been shown to produce a pathophysiological response primarily involving swelling of astroglial cells as a secondary, inhibitable process. At the molecular level, the sequence appears to be: trauma, elevation of extracellular $K^+$ and/or release of neurotransmitters, edema, hypoxia and necrosis. Astroglial swelling results directly from a $K^+$-dependent, cation-coupled, chloride transport from the extra-cellular into the intracellular compartment with a concomitant movement of an osmotic equivalent of water. Thus, an agent that specifically blocks chloride transport in the astroglia is expected to block the edema caused by trauma and other insults to the brain. It is also important that such chloride transport inhibitors be free or relatively free of side effects, particularly those characteristics of many chloride transport inhibitors, such as diuretic properties. Compounds of the type illustrated by Formula I exhibit the desired effects on brain edema and are relatively free of renal effects.

That this approach is valid has been demonstrated by the correlation of the in vitro astroglial edema inhibiting effects of chloride transport inhibitors with their ability to reduce the mortality of animals receiving experimental in vivo head injury. As a final proof, one compound (ethacrynic acid) which exhibited activity both in vitro and in vivo assays was effective in reducing mortality in clinical cases of head injury. These studies are described in the Journal of Medicinal Chemistry, Volume 25, page 567 (1982), which is hereby incorporated by reference.

Three major biological assays can be used to demonstrate biological activity of the compounds. The (1) in vitro cat cerebrocortical tissue slice assay, (2) the in vitro primary rat astrocyte culture assay and (3) the in vivo cat head injury assay. The first assay, the in vitro cat cerebrocortical tissue slice assay has been described by Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 347, by Bourke, R. S.; Kimelberg, H. K.; Daze, M. A. in Brain Res. 1978, 154, 196, and by Bourke, R. S.; Kimelberg, H. K.; Nelson, L. R. in Brain Res. 1976, 105, 309. This method constitutes a rapid and accurate method of determining the intrinsic chloride inhibitory properties of the compounds of the invention in the target tissue.

The second assay method involves the in vitro primary rat astrocyte assay. The method has been described by Kimelberg, H. K.; Biddlecome, S.; Bourke, R. S. in Brain Res. 1979, 173, 111, by Kimelberg, H. K.; Bowman, C.; Biddlecome, S.; Bourke, R. S., in Brain Res. 1979, 177, 533, and by Kimelberg, H. K.; Hirata, H. in Soc. Neurosci. Abstr. 1981, 7, 698. This method is used to confirm the chloride transport inhibiting properties of the compounds in the pure target cells, the astrocytes.

The third assay method, the in vivo cat head injury assay has been described by Nelson, L. R.; Bourke, R. S.; Popp, A. J.; Cragoe, E. J. Jr.; Signorelli, A.; Foster, V. V.; Creel, in Marshall, L. F.; Shapiro, H. M.; Smith, R. W. In "Seminars in Neurological Surgery: Neural Trauma"; Popp, A. J.; Bourke, R. S.; Nelson, L. R.; Kimelberg, H. K., Eds.; Raven Press: New York, 1979; p. 297.

This assay consists of a highly relevant brain injury in cats which is achieved by the delivery of rapid repetitive acceleration-deceleration impulses to the animal's head followed by exposure of the animals to a period of hypoxia. The experimental conditions of the assay can be adjusted so that the mortality of the control animals falls in the range of about 25 to 75%. Then, the effect of the administration of compounds of this invention in reducing the mortality over that of the control animals in concurrent experiments can be demonstrated.

Using the in vitro cat cerebrocortical tissue slice assay, described in Example 1, compounds of the present invention can be tested for activity. This test provides the principal in vitro evaluation and consists of a determination of concentration vs. response curve. The addition of $HCO_3$[31] to isotonic, $K^+$-rich saline-glucose incubation media is known to specifically stimulate the transport of $Cl^-$ coupled with $Na^+$ and an osmotic equivalent of water in incubating slices of mammalian cerebral cortex. Experiments have demonstrated that the tissue locus of swelling is an expanded astroglial compartment. Thus, the addition of $HCO_3^-$ to incubation media stimulates statistically significant and comparable increases in cerebrocortical tissue swelling and ion levels. After addition of drug to the incubation media, detailed drug concentration-response curves are then obtained.

The following Examples are included to illustrate the in vitro cerebrocortical tissue slice assay, the preparation of representative compounds of Formula I and representative dosage forms of these compounds. It is intended that the specification and Examples be considered as exemplary only, with the true scope and spirit of the invention being indicated by the following claims.

EXAMPLE 1

In Vitro Cerebrocortical Tissue Slice Assay

Adult cats of 2-3 kg body weight are employed in tissue slice studies. Prior to sacrifice, the animals are anesthetized with ketamine hydrochloride (Ketaset), 10 mg/kg im. Eight (three control, five experimental) pial surface cerebrocortical tissue slices (0.5-mm thick; approximately 150 initial fresh weight) are cut successively with a calibrated Stadie-Riggs fresh tissue microtome without moistening and weighed successively on a torsion balance. During the slice preparation all operations except weighing are confined to a humid chamber. Each slice is rapidly placed in an individual Warburg flask containing 2 ml of incubation medium at room temperature. The basic composition of the incubation media, in millimoles per liter, is as follows: glucose, 10; $CaCl_2$, 1.3; $MgSO_4$, 1.2; $KHSO_4$, 1.2; Hepes (N-2-hydroxy-ethylpiperazine-N'-2-ethanesulfonic acid, titrated with NaOH to pH 7.4), 20. Except when adding $HCO_3^-$, the osmolarity of the media is maintained isomotic (approximately 285 mOsm/L) by reciprocal changes of $Na^+$ or $K^+$ to achieve a concentration of $K^+$ of 27 mM. The basic medium is bubbled for 30 minutes with 100% $O_2$ before use. When added, $NaHCO_3$ or triethylammonium bicarbonate (TEAB) is initially present in the sidearm of each flask at an initial concentration of 50 mM in 0.5 ml of complete medium. Nonbicarbonate control slices are incubated at 37° C. in 2.5 ml of basic medium for 60 minutes. Bicarbonate control slices are similarly incubated for an initial 20 minutes at 37° C. in 2.0 ml of basic medium to which is added from the sidearm an additional 0.5 ml of incubation medium containing 50 mM $HCO_3^-$, which, after mixing, results in a $HCO_3^-$ concentration of 10 mM and a total volume of 2.5 ml. The incubation is continued for an additional 40 minutes. The various compounds to be tested are dissolved by forming the sodium salts by treatment with a molar equivalent of NaHCO$_3$ and diluting to the appropriate concentrations. Just prior to incubation, all flasks containing HCO$_3^-$ are gassed for 5 minutes with 2.5% CO$_2$/97.5% O$_2$ instead of 100% O$_2$.

Following the 60-minute incubation period, tissue slices are separated from incubation medium by filtration, reweighed, and homogenized in 1N HClO$_4$ (10% w/v) for electrolyte analysis. The tissue content of ion is expessed in micromoles per gram initial preswelling fresh weight. Control slice swelling is expressed as microliters per gram initial preswelling fresh weight. The effectiveness of an inhibitor at a given concentration is measured by the amount of HCO$_3^-$-stimulated swelling that occurred in its presence, computed as a percent of the maximum possible. Tissue and media Na$^+$ and K$^+$ are determined by emission flame photometry with Li$^+$ internal standard; Cl$^-$ is determined by amperometric titration. Tissue viability during incubation is monitored by manometry.

EXAMPLE 2

Preparation of
[(3,4-dichloro-6,7,8,8a,9,10-hexahydro-6-oxo-8a-propyl-2-phenanthrenyl)oxy]acetic acid Step A: 2-Bromo-7,8-dichloro-6-methoxy-1-tetralone 7,8-Dichloro-6-methoxy-1-tetralone (2.7 g, 0.011 mole) was suspended in acetic acid (45 ml) warmed slightly with stirring, and 0.57 ml of bromine in 5 ml of acetic acid was added over a 20 minute time period. The reaction mixture was stirred for 10 minutes, and then poured into 200 ml of stirred ice water. A white solid was filtered from the reaction mixture, dissolved in ether (75 ml), washed with brine, dried over MgSO$_4$, evaporated in vacuo and directly used in the next step.

Step B:
7,8-Dichloro-6-methoxy-2-propylidene-1-tetralone

2-Bromo-7,8-dichloro-6-methoxy-1-tetralone (0.01 mole), benzene (50 ml), dimethyl sulfoxide (5 ml), propionaldehyde (3 ml, 0.04 mole) and zinc dust (6.5 g, 0.1 mole) were stirred under nitrogen. After 48 hours, the reaction mixture was poured into ice water, washed with brine, dried over MgSO$_4$ and filtered, treated with 300 mg of para-toluene sulfonic acid, then refluxed for 15 minutes. The reaction mixture was cooled, filtered, evaporated and chromatographed on 140 g SiO$_2$ (ethyl acetatehexane 3:7) to yield 1.25 g of 7,8-dichloro-6-methoxy-2-propylidene-1-tetralone which was directly used in Step C.

Step C: 7,8-Dichloro-6-methoxy-2-propyl-1-tetralone 7,8-Dichloro-6-methoxy-2-propylidene-1-tetralone (1.1 g) in 50 ml of 2-propanol and 150 mg of 5% Pd/C catalyst, were placed in a Parr apparatus and hydrogenated at 30 psi for 20 minutes. The reaction mixture was warmed slightly, the catalyst filtered, rinsed with 2-propanol, evaporated to dryness and chromatographed on 40 g SiO$_2$ (ethyl acetae-hexane, 1:3) to yield 680 mg of 7,8-dichloro-6-methoxy-2-propyl-1-tetralone which melted at 127°–9° C. after recrystallization from ethyl acetate.

Analysis for C$_{14}$H$_{16}$Cl$_2$O$_2$: Calc: C, 58.55; H, 5.62. Found: C, 58.32; H, 5.73.

Step D:
2-(3-Oxobutyl)-7,8-dichloro-6-methoxy-2-propyl-1-tetralone

In an atmosphere of dry argon, sodium hydride (115.2 mg, 4.8 mmole) was suspended in a mixture of dimethylformamide (1 ml) and toluene (1 ml). The mixture was stirred and heated to 35° C. while 7,8-dichloro-6-methoxy-2-propyl-1-tetralone (700 mg, 2.58 mmole) in a mixture of dimethylformamide (2 ml) and toluene (4 ml) was added dropwise over a period of 20 minutes and the temperature rose to 45°–50° C. There was a slow evolution of hydrogen during the reaction. The reaction was stirred for an additional 10 minutes, then cooled to 35° C. and 1,3-dichloro-2-butene (406 mg, 3.25 mmoles) in toluene (1 ml) was added dropwise followed by heating at 50° for one hour. The mixture was then cooled to room temperature and poured with stirring into ice water (50 ml). The organic layer was separated washed first with water and then with brine and dried over MgSO$_4$. The organic layer was evaporated in vacuo to give 1.1 g of 2-(3-chloro-2-butenyl)-7,8-dichloro-6-methoxy-2-propyl-tetralone which was dissolved in methylene chloride (10 ml) and added with stirring to cold mixture of concentrated sulfuric acid (12 ml) and methylene chloride (12 ml) while cooling in an ice bath. The mixture was stirred for 30 minutes and then poured into a mixture of ice (50 g) and methylene chloride (50 ml). The organic layer was separated and the aqueous layer extracted with methylene chloride. The combined organic layers were diluted with ether (100 ml), washed first with water, then with brine and finally dried over MgSO$_4$. The solvents were removed by evaporation in vacuo to give a residue of 900 mg of 2-(3-oxobutyl)-7,8-dichloro-6-methoxy-2-propyl-1-tetralone.

Step E:
3,4-Dichloro-6,7,8,8a,9,10-hexahydro-2-methoxy-6-oxo-8a-propylphenanthrene 2-(3-Oxobutyl)-7,8-dichloro-6-methoxy-2-propyl-1-tetralone (700 mg), ethanol (25 ml), water (6 ml) and 10N sodium hydroxide solution (200 μl) were combined and stirred at room temperature for 96 hours. The reaction mixture was evaporated in vacuo at 30° C. treated with water, extracted two times with 100 ml of ether, washed with water, brine dried over MgSO$_4$, evaporated in vacuo, and chromatographed on 25 g of SiO$_2$ (ethyl acetate-hexane; 1:2) to give 350 mg of 3,4-Dichloro-6,7,8,8a,9,10-hexahydro-2-methoxy-6-oxo-8a-propylphenanthrene which was used in the next step.

STEP F:
3,4-Dichloro-6,7,8,8a,9,10-hexahydro-2-hydroxy-6-oxo-8a-propylphenanthrene Pyridine hydrochloride (20 g, 175 mmole) was heated to 180° C. and 3,4-dichloro-6,7,8,8a,-9,10-hexahydro-2-methoxy-6-oxo-8a-propylphenanthrene (340 mg) added. The reaction mixture was stirred in an oil bath at 190° C. for 1½ hours, poured into ice water, extracted with ether, washed with water and brine, dried over MgSO$_4$ and evaporated in vacuo to give a red oil consisting of 3,4-dichloro-6,7,8,8a,9,10-hexahydro-2-hydroxy-6-oxo-8a-propylphenanthrene, which was used in Step G with out further purification.

Step G:
[(3,4-Dichloro-6,7,8,8a,9,10-hexahydro-6-oxo-8a-propyl-2-phenanthrenyl)oxy]acetic acid In an atmosphere of nitrogen, 3,4-dichloro-6,7,8,8a,9,10-hexahydro-2-hydroxy-6-oxo-8a-propylphenanthrene (280 mg, 0.86 mmole), potassium carbonate (150 mg, 1.08 mole) and dimethylformamide (5 ml), were heated to 55° C. with stirring. Ethyl bromoacetate (226 mg, 1.35 mmole) was added and stirred at 60°–65° C. for 1½ hours. The reaction mixture was poured into ice water, extracted with ether, washed with water then brine, dried over MgSO4 and evaporated in vacuo to give 350 mg of an oil consisting of ethyl [(3,4-dichloro-6,7,8,8a,9,10-hexahydro-2-hydroxy-6-oxo-8a-propyl-2-phenanthrenyl)oxy]acetate. The oil was dissolved in methanol (15 ml) water (1 ml) and 10N sodium hydroxide (1 ml). The mixture was stirred at room temperature for 45 minutes. Then the reaction mixture was poured into a mixture of ice water and hydrochloric acid and extracted with ether. The ether layer was separated, washed twice with water, followed by brine, then dried over MgSO4 and evaporated in vacuo to yield a 250 mg of yellow foam. The residue was chromatographed on 25 g SiO2 (dichloromethane-tetrahydrofuran-acetic acid, 50:1:1), pertinent fractions evaporated, and triturated with 2 ml ether to yield 110 mg of [(3,4-dichloro-6,7,8,8a,9,10-hexahydro-6-oxo-8a-propyl-2-phenanthrenyl)oxy]acetic acid which melted at 193°–4° C.

Analysis for $C_{12}H_{20}Cl_2O_4$: Calc: C, 59.54; H, 5.26. Found: C, 59.56; H, 5.51.

EXAMPLE 3

Resolution of [(3,4-Dichloro-6,7,8,8a,9,10-hexahydro-6-oxo-8a-propyl-2-phenanthrenyl)oxy]acetic acid Racemic [(3,4-dichloro-6,7,8,8a,9,10-hexahydro-6-oxo-8a-propyl-2-phenanthrenyl)oxy]acetic acid (3.51 g, 10 mmole) in acetonitrile is heated to boiling and cinchonine (2.95 g, 10 mmole) is added. The solution is stirred and cooled at 5° C. for 48 hours and the solid (A) that separates is removed by filtration, washed with acetonitrile and the filtrate (B) saved. The solid (A) is recrystallized from acetonitrile and the product removed by filtration, dried, treated with 1 normal hydrochloric acid (50 ml) and extracted with a mixture of 20% tetrahydrofuran in ether. The combined organic extracts are dried over MgSO4; the solvents removed by evaporation in vacuo and the residue recrystallized from butyl chloride to give the (+) enantiomer of [(3,4-dichloro-6,7,8,8a,9,10-hexahydro-6-oxo-8a-propyl-2-phenanthrenyl)oxy]acetic acid.

The filtrate (B) is evaporated in vacuo, treated with 2 normal hydrochloric acid (45 ml), extracted with 20% tetrahyrofuran in ether and the organic extract dried over MgSO4. The solvent is evaporated in vacuo and the residue dissolved in acetonitrile (250 ml), heated to boiling and cinchonidine (2.95 g, 10 mmole) is added. The solution is cooled to 5° C. and stirred for 48 hours. The solid that separates is removed by filtration, dried and treated as described above for the (+) isomer to obtain the (−) enantiomer of [(3,4-dichloro-6,7,8,8a,9,10-hexahydro-6-oxo-8a-propyl-2-phenanthrenyl)oxy]acetic acid.

EXAMPLE 4

2-[(3,4-Dichloro-6,7,8,8a,9,10-hexahydro-6-oxo-8a-propyl-2-phenanthrenyl)oxy]ethanimidamide hydrochloride Step A:
2-[(3,4-Dichloro-6,7,8,8a,9,10-hexahydro-6-oxo-8a-propyl-2-phenanthrenyl)oxy]acetonitrile A stirred mixture of 3,4-dichloro-6,7,8,8a,9,10-hexahydro-2-hydroxy-6-oxo-8a-propylphenanthrene (0.4 g, 1.22 mmole), potassium carbonate (0.2 g, 1.45 mmole) and chloroacetonitrile (160 μl, 1.78 mmole) in dimethylformamide (7 ml) is heated at 65° C. for 2 hours, poured into ice water, extracted with ether, washed with water, brine, dried over MgSO4 and evaporated in vacuo. Trituration of the residual oil with butyl chloride give 2-[(3,4-Dichloro-6,7,8,8a,9,10-hexahydro-6-oxo-8a-propyl-2-phenanthrenyl)oxy]acetonitrile which is removed by filtration, and dried.

Step B:
2-[(3,4-Dichloro-6,7,8,8a,9,10-hexahydro-6-oxo-8a-propyl-2-phenanthrenyl)oxy]ethanimidamide hydrochloride To a solution of 2-[(3,4-Dichloro-6,7,8,8a,9,10-hexahydro-6-oxo-8a-propyl-2-phenanthrenyl)oxy]acetonitrile (200 mg, 0.549 mmole) in methanol (3 ml) is added sodium methoxide (10 mg). After stirring for 1 hour ammonium chloride (53.5 mg, 1 mmole) is added and stirring is continued for 2 hours. The reaction mixture is poured into ice water containing 0.5 ml of 10N sodium hydroxide extracted with ether, washed with water dried over potassium carbonate, filtered and acidified with 10N ethanolic hydrochloric acid to precipitate 2-[(3,4-Dichloro-6,7,8,8a,8,10-hexahydro-6-oxo-8a-propyl-2-phenanthrenyl)oxy]ethanimidamide hydrochloride.

EXAMPLE 5

(+)2-[(3,4-Dichloro-6,7,8,8a,9,10-hexahydro-6-oxo-8a-propyl-2-phenanthrenyl)oxy]ethanimidamide hydrochloride Step A: (+) 3,4-Dichloro-6,7,8,8a,9,10-hexahydro-2-hydroxy-6-oxo-8a-propylphenanthrene Pyridine hydrochloride (20 g, 173 mmole) is melted and heated to 190° C. and then (+) [(3,4-dichloro-6,7,8,8a,9,10-hexahydro-6-oxo-8a-propyl-2-phenanthrenyl)oxy]acetic acid (Example 3) (325 mg, 1 mmole) is added and stirred for 15 minutes at 190° C. The mixture is poured into crushed ice (200 g) and the product extracted with ether. The organic extract is washed with water, then with brine and dried over MgSO4. Evaporation of the solvent gave (+)3,4-dichloro-6,7,8,8a,9,10-hexahydro-2-hydroxy-6-oxo-8a-propylphenanthrene.

Step B:
(+)2-[(3,4-Dichloro-6,7,8,8a,9,10-hexahydro-6-oxo-8a-propyl-2-phenanthrenyl)oxy]acetonitrile By carrying out the reaction as described in Example 4, Step A, except that the racemic 3,4-dichloro-6,7,8,8a,9,10-hexahydro-2-hydroxy-6-oxo-8a-propylphenanthrene is replaced by an equal amount of (+)3,4-dichloro-6,7,8,8a,9,10-hexahydro-2-hydroxy-6-oxo-8a-propylphenanthrene, there is obtained (+)2-[(3,4- dichloro-6,7,8,8a,9,10-hexahydro-6-oxo-8a-propyl-2-phenanthrenyl)oxy]acetonitrile.

Step C:
(+)2-[(3,4-Dichloro-6,7,8,8,9,10-hexahydro-6-oxo-8a-propyl-2-phenanthrenyl)oxy]ethanimidamide hydrochloride By carrying out the reaction as described in Example 4, Step B, except that the racemic 2-[(3,4-dichloro-6,7,8,8a,9,10-hexahydro-6-oxo-8a-propyl-2-phenanthrenyl)oxy]acetonitrile is replaced by an equal amount of (+)2-[(3,4-dichloro-6,7,8,8a,9,10-hexahydro-8a-propyl-2-phenanthrenyl)oxy]acetonitrile, there is obtained (+)2-[(3,4-dichloro-6,7,8,8a,9,10-hexahydro-6-oxo-8a-propyl-2-phenanthrenyl)oxy]ethanimidamide hydrochloride.

EXAMPLE 6
(−)2-[(3,4-Dichloro-6,7,8,8a,9,10-hexahydro-6-oxo-8a-propyl-2-phenanthrenyl)oxy]ethanimidamide hydrochloride

Step A:
(−)3,4-Dichloro-6,7,8,8a,9,10-hexahydro-2-hydroxy-6-oxo-8a-propylphenanthrene Pyridine hydrochloride (20 g, 173 mmole) is melted and heated to 190° C. and then (−) [(3,4-dichloro-6,7,8,8a,9,10-hexahydro-6-oxo-8a-propyl-2-phenanthrenyl)oxy]acetic acid (Example 3) (325 mg, 1 mmole) is added and stirred for 15 minutes at 190°. The mixture is poured into crushed ice (200 g) and the product extracted with ether. The organic extract is washed with water, then with brine and dried over MgSO$_4$. Evaporation of the solvent gave (−)3,4-dichloro-6,7,8,8a,9,10-hexahydro-2-hydroxy-6-oxo-8a-propylphenanthrene.

Step B:
(−)2-[(3,4-Dichloro-6,7,8,8a,9,10-hexahydro-6-oxo-8a-propyl-2-phenanthrenyl)oxy]acetonitrile By carrying out the reaction as described in Example 4, Step A, except that the racemic 3,4-dichloro-6,7,8,8a,9,10-hexahydro-2-hydroxy-6-oxo-8a-propylphenanthrene is replaced by an equal amount of (−)3,4-dichloro-6,7,8,8a,9,10-hexahydro-2-hydroxy-6-oxo-8a-propylphenanthrene, there is obtained (−)2-[(3,4,-dichloro-6,7,8,8a,9,10-hexahydro-6-oxo-8a-propyl-2-phenanthrenyl)oxy]acetonitrile.

Step C:
(−)2-[(3,4-Dichloro-6,7,8,8a,9,10-hexahydro-6-oxo-8a-propyl-2-phenanthrenyl)oxy]ethanimidamide hydrochloride By carrying out the reaction as described in Example 4, Step B, except that the racemic 2-[3,4-dichloro-6,7,8,8a,9,10-hexahydro-6-oxo-8a-propyl-2-phenanthrenyl)oxy]acetonitrile is replaced by an equal amount of (−)-2-[(3,4-dichloro-6,7,8,8a,9,10-hexahydro-8a-propyl-2-phenanthrenyl)oxy]acetonitrile, there is obtained (−)-2-[(3,4-dichloro-6,7,8,8a,9,10-hexahydro-6-oxo-8a-propyl-2-phenanthrenyl)oxy]ethanimidamide hydrochloride.

EXAMPLE 7
1-Carboxy-1-methylethyl [(3,4-dichloro-6,7,8,8a,9,10-hexahydro-6-oxo-8a-propyl-2-phenanthrenyl)oxy]acetate

[(3,4-Dichloro-6,7,8,8a,9,10-hexahydro-6-oxo-8a-propyl-2-phenanthrenyl)oxy]acetic acid (351 mg, 1 mmole) is dissolved in tetrahydrofuran (10 ml) and treated with 1,1′-carbonyldiimidazole (160 mg, 1 mmole) and the mixture stirred at room temperature for an hour. 2-Hydroxy-2-methylpropionic acid (105 mg, 1 mmole) is added and the mixture stirred for 18 hours at room temperature. The solvent is removed by evaporation in vacuo and the residue purified by column chromatography on silica gel using dichloromethane/tetrahydrofuran/acetic acid 100/2/1, v.v.v. to give 1-carboxy-1-methylethyl [(3,4-dichloro-6,7,8,8a,9,10-hexahydro-6-oxo-8a-propyl-2-phenanthrenyl)oxy]acetate.

EXAMPLE 8
1-Carboxy-1-methylethyl (+)[(3,4-dichloro-6,7,8,8a,9,10-hexahydro-6-oxo-8a-propyl-2-phenanthrenyl)oxy]acetate (+)[(3,4-Dichloro-6,7,8,8a,9,10-hexahydro-6-oxo-8a-propyl-2-phenanthrenyl)oxy]acetic acid (351 mg, 1 mmole) is dissolved in tetrahydrofuran (10 ml) and treated with 1,1′-carbonyldiimidazole (160 mg, 1 mmole) and the mixture stirred at room temperature for an hour. 2-Hydroxy-2-methylpropionic acid (105 mg, 1 mmole) is added and the mixture stirred for 18 hours at room temperature. The solvent is removed by evaporation in vacuo and the residue purified by column chromatography on silica gel using dichloromethane/tetrahydrofuran/acetic acid (100/2/1, v.v.v.) to give 1-carboxy-1-methylethyl (+)[(3,4-dichloro-6,7,8,8a,9,10-hexahydro-6-oxo-8a-propyl-2-phenanthrenyl)oxy]acetate.

EXAMPLE 9
Parenteral Solution of [(3,4-dichloro-6,7,8,8a,9,10-hexahydro-6-oxo-8a-propyl-2-phenanthrenyl)oxy]acetic acid

[(3,4-Dichloro-6,7,8,8a,9,10-hexahydro-6-oxo-8a-propyl-2-phenanthrenyl)oxy]acetic acid (500 mg) is dissolved by stirring and warming with 0.25N sodium bicarbonate solution (5.4 ml). The solution is diluted to 10 ml and sterilized by filtration. Allthe water that is used in the preparation is pyrogen-free. The concentration of the active agent in the final solution is 5%.

EXAMPLE 10
Parenteral Solution of (+)[(3,4-dichloro-6,7,8,8a,9,10-hexahydro-6-oxo-8a-propyl-2-phenanthrenyl)oxy]acetic acid (+)[(3,4-Dichloro-6,7,8,8a,9,10-hexahydro-6-oxo-8a-propyl-2-phenanthrenyl)oxy]acetic acid (500 mg) is dissolved by stirring and warming wih 0.25N sodium bicarbonate solution (5.4 ml). The solution is diluted to 10 ml and sterilized by filtration. All the water that is used in the preparation is pyrogen-free. The concentration of the active agent in the final solution is 5%.

EXAMPLE 11
Dry-Filled Capsules Containing 100 mg of Active Ingredient Per Capsule

| | Per Capsule |
|---|---|
| [(3,4-dichloro-6,7,8,8a,9,10-hexahydro-6-oxo-8a-propyl-2-phenanthrenyl)oxy]acetic acid | 100 mg |
| Lactose | 99 mg |
| Magnesium Stearate | 1 mg |

-continued

| | Per Capsule |
|---|---|
| Capsule (Size No. 1) | 200 mg |

[(3,4-Dichloro-6,7,8,8a,9,10-hexahydro-6-oxo-8a-propyl-2-phenanthrenyl)oxy]acetic acid is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 12

Dry-Filled Capsules Containing 100 mg of Active Ingredient Per Capsule

| | Per Capsule |
|---|---|
| (+)[(3,4-dichloro-6,7,8,8a,9,10-hexahydro-6-oxo-8a-propyl-2-phenanthrenyl)oxy]acetic acid | 100 mg |
| Lactose | 99 mg |
| Magnesium Stearate | 1 mg |
| Capsule (Size No. 1) | 200 mg |

(+)[(3,4-Dichloro-6,7,8,8a,9,10-hexahydro-6-oxo-8a-propyl-2-phenanthrenyl)oxy]acetic acid is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 13

Parenteral Solution of 2-[(3,4-dichloro-6,7,8,8a,9,10-hexahydro-6-oxo-8a-propyl-2-phenanthrenyl)oxy]ethanimidamide hydrochloride 2-[(3,4-Dichloro-6,7,8,8a,9,10-hexahydro-6-oxo-8a-propyl-2-phenanthrenyl)oxy]ethanimidamide hydrochloride (552 mg) is dissolved by stirring and warming with water (5 ml). The solution is diluted to 10 ml and sterilized by filtration. All the water that is used in the preparation is pyrogen-free. The concentration of the active agent in the final solution is 5% calculated as free base.

EXAMPLE 14

Parenteral Solution of (+)2-[(3,4-dichloro-6,7,8,8a,9,10-hexahydro-6-oxo-8a-propyl-2-phenanthrenyl)oxy]ethanimidamide hydrochloride (+)2-[(3,4-Dichloro-6,7,8,8a,9,10-hexahydro-6-oxo-8a-propyl-2-phenanthrenyl)oxy]ethanimidamide hydrochloride (552 mg) is dissolved by stirring and warming with water (5 ml). The solution is diluted to 10 ml and sterilized by filtration. All the water that is used in the preparation is pyrogen-free. The concentration of the active agent in the final solution is 5% calculated as free base.

Similar parenteral solutions can be prepared by replacing the active ingredient of this Example by and of the other compounds of this invention.

EXAMPLE 15

Dry-Filled Capsules Containing 100 mg of Active Ingredient (free base) Per Capsule

| | Per Capsule |
|---|---|
| 2-[(3,4-dichloro-6,7,8,8a,9,10-hexahydro-6-oxo-8a-propyl-2-phenanthrenyl)oxy]ethanimidamide hydrochloride | 110.4 mg |
| Lactose | 88.6 mg |
| Magnesium Stearate | 1 mg |
| Capsule (Size No. 1) | 200 mg |

2-[(3,4-Dichloro-6-7,8,8a,9,10-hexahydro-6-oxo-8a-propyl-2-phenanthrenyl)oxy]ethanimidamide hydrochloride is reduced to a No. 60 powder and then the lactose and magnesium stearate are passed through a No. 60 bolting cloth onto the powder and the combined ingredients admixed for 10 minutes and then filled into a No. 1 dry gelatin capsule.

EXAMPLE 16

Dry-Filled Capsules Containing 100 mg of Active Ingredient (free base) Per Capsule

| | Per Capsule |
|---|---|
| (+)2-[(3,4-dichloro-6,7,8,8a,9,10-hexahydro-6-oxo-8a-propyl-2-phenanthrenyl)oxy]ethanimidamide hydrochloride | 110.4 mg |
| Lactose | 88.6 mg |
| Magnesium Stearate | 1 mg |
| Capsule (Size No. 1) | 200 mg |

(+)2-[(3,4-Dichloro-6,7,8,8a,9,10-hexahydro-6-oxo-8a-propyl-2-phenanthrenyl)oxy]ethanimidamide hydrochloride is reduced to a No. 60 powder and then the lactose and magnesium stearate are passed through a No. 60 bolting cloth onto the powder and the combined ingredients admixed for 10 minutes and then filled into a No. 1 dry gelatin capsule.

Similar capsules can be prepared by replacing the active ingredient of this Example by any of the other compounds of thiis invention.

What is claimed is:

1. A compound of the formula:

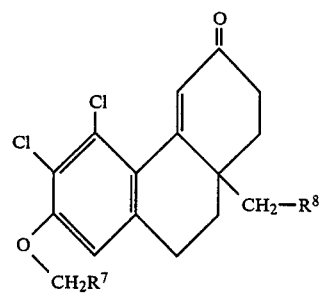
(II)

wherein:
$R^7$ is COOH, COOR$^9$ or

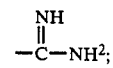

$R^8$ is H or lower alkyl, branched or unbranched, containing from 1 to 5 carbon atoms;

$R^9$ is a carboxyalkyl group containing from 2 to 6 carbon atoms.

2. A compound according to claim 1, which is
[(3,4-dichloro-6,7,8,8a,9,10-hexahydro-6-oxo-8a-propyl-2-phenanthrenyl)oxy]acetic acid;

2-[(3,4-dichloro-6,7,8,8a,9,10-hexahydro-6-oxo-8a-propyl-2-phenanthrenyl)oxy]ethanimidamide;

1-carboxy-1-methylethyl[(3,4-dichloro-6,7,8,8a,9,10-hexahydro-6-oxo-8a-propyl-2-phenanthrenyl)oxy]acetate.

3. A compound according to claim 2, which is the pure racemate.

4. A compound according to claim 3, which is the (+)-enantiomer.

5. A compound according to claim 3, which is the (−)-enantiomer.

6. A pharmaceutical composition which comprises a pharmaceutical carrier and an effective amount of a compound according to claim 2.

7. A method which comprises administering to a person with brain injury and an effective amount of a compound according to claim 1.

* * * * *